(12) United States Patent
Yamada et al.

(10) Patent No.: US 11,653,819 B2
(45) Date of Patent: May 23, 2023

(54) ENDOSCOPE AND ENDOSCOPE SYSTEM

(71) Applicant: OLYMPUS CORPORATION, Tokyo (JP)

(72) Inventors: Norihito Yamada, Tokyo (JP); Madoka Saito, Yokohama (JP); Shigetoshi Futami, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 315 days.

(21) Appl. No.: 16/939,585

(22) Filed: Jul. 27, 2020

(65) Prior Publication Data
US 2020/0352428 A1 Nov. 12, 2020

Related U.S. Application Data

(63) Continuation of application No. PCT/JP2018/030509, filed on Aug. 17, 2018.

(30) Foreign Application Priority Data

Mar. 12, 2018 (JP) .............................. JP2018-044032

(51) Int. Cl.
*A61B 1/00* (2006.01)
*A61B 1/04* (2006.01)
*A61B 1/12* (2006.01)

(52) U.S. Cl.
CPC ...... *A61B 1/00124* (2013.01); *A61B 1/00029* (2013.01); *A61B 1/00036* (2013.01); *A61B 1/044* (2022.02); *A61B 1/128* (2013.01)

(58) Field of Classification Search
None
See application file for complete search history.

(56) References Cited

U.S. PATENT DOCUMENTS 5,609,561 A * 3/1997 Uehara .................. A61B 1/042
348/75
2004/0201743 A1* 10/2004 Amling .............. H04N 5/23225
348/E5.042

(Continued)

FOREIGN PATENT DOCUMENTS

JP 2005-040327 A 2/2005
JP 2006-158484 A 6/2006

(Continued)

OTHER PUBLICATIONS

International Search Report dated Nov. 13, 2018 issued in PCT/JP2018/030509.

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope provides a connector substrate of an endoscope connector to be connected to a processor with a temperature sensor for directly measuring a temperature of the connector substrate, performs control to restrict a power supply (in other words, limit and stop a power supply) from an endoscope power supply circuit according to the measured temperature of the connector substrate (in other words, the endoscope connector), and thereby appropriately manages the temperature of the endoscope connector in the endoscope.

20 Claims, 15 Drawing Sheets

(56) References Cited

U.S. PATENT DOCUMENTS

| | | | |
|---|---|---|---|
| 2005/0222559 A1* | 10/2005 | Shiono | A61B 18/24 606/12 |
| 2011/0190746 A1* | 8/2011 | Rink | A61B 18/22 606/11 |
| 2012/0232534 A1* | 9/2012 | Rink | A61B 18/24 606/3 |
| 2013/0030248 A1 | 1/2013 | Matsumaru | |
| 2013/0116507 A1* | 5/2013 | Segawa | A61B 1/051 600/109 |
| 2013/0154509 A1* | 6/2013 | Yabe | A61B 1/0669 315/297 |
| 2013/0169775 A1* | 7/2013 | Ono | A61B 1/128 348/68 |
| 2013/0345510 A1* | 12/2013 | Hadani | A61B 1/018 600/113 |
| 2014/0307071 A1* | 10/2014 | Hirosawa | H04N 5/363 348/65 |
| 2015/0080657 A1* | 3/2015 | Ide | A61B 1/127 600/117 |
| 2015/0148603 A1* | 5/2015 | Holste | A61B 1/128 600/109 |
| 2015/0201827 A1* | 7/2015 | Sidar | A61B 1/128 348/65 |
| 2015/0223867 A1* | 8/2015 | Brandt | A61B 18/1442 606/34 |
| 2015/0223868 A1* | 8/2015 | Brandt | A61B 18/1445 606/40 |
| 2015/0297070 A1* | 10/2015 | Ide | A61B 1/0008 600/109 |
| 2015/0313454 A1* | 11/2015 | Ide | A61B 1/0008 600/129 |
| 2017/0202445 A1* | 7/2017 | Sakai | A61B 1/051 |
| 2017/0288688 A1* | 10/2017 | Maki | H01S 5/183 |
| 2018/0228357 A1* | 8/2018 | Fujii | G01K 15/007 |
| 2019/0356829 A1* | 11/2019 | Sidar | H04N 7/185 |

FOREIGN PATENT DOCUMENTS

| | | |
|---|---|---|
| JP | 2007-029452 A | 2/2007 |
| JP | 2011-083454 A | 4/2011 |
| JP | 2013-027418 A | 2/2013 |
| WO | WO 2013/125114 A1 | 8/2013 |

\* cited by examiner

US 11,653,819 B2

ENDOSCOPE AND ENDOSCOPE SYSTEM

CROSS REFERENCE TO RELATED APPLICATION

This application is a continuation application of PCT/JP2018/030509 filed on Aug. 17, 2018 and claims benefit of Japanese Application No. 2018-044032 filed in Japan on Mar. 12, 2018, the entire contents of which are incorporated herein by this reference.

BACKGROUND OF THE INVENTION

1. Field of the Invention

The present invention relates to an endoscope and an endoscope system including a connector attachable/detachable to/from an external apparatus.

2. Description of the Related Art

Conventionally, endoscopes capable of observing organs within a body cavity or the like by inserting an elongated insertion portion into the body cavity have been widely used in a medical field.

For such endoscopes, it is necessary to take measures against heat generation at a distal end portion in particular. As one measure, for example, Japanese Patent Application Laid-Open Publication No. 2013-27418 discloses a technique of an endoscope incorporating a first circuit section including an image pickup apparatus including an image pickup device and peripheral circuits and a first regulator as a power supply circuit in a distal end portion of the endoscope, and incorporating a second circuit section (connector substrate) including a second regulator that supplies power to the first regulator in a connector, in which when temperature detection means disposed in the distal end portion or an overcurrent detection function of the regulator or the like detects at least one of a temperature abnormality and an overcurrent at the distal end portion, a power supply to the distal end portion is stopped by stopping at least one of output of the first regulator and output of the second regulator.

SUMMARY OF THE INVENTION

An endoscope according to an aspect of the present invention is an endoscope including an insertion portion including a distal end portion, a substrate incorporated in an exterior member provided closer to a proximal end side than the insertion portion, a power supply circuit and an electronic part being mounted on the substrate, the substrate being configured to receive a power supply and a control signal from an external apparatus and supply power from the power supply circuit to an image pickup device on a distal end side and the electronic part, a temperature sensor configured to measure a temperature of the substrate and a power supply restriction circuit configured to restrict the power supply from the power supply circuit according to the temperature of the substrate measured by the temperature sensor.

An endoscope system according to another aspect of the present invention is an endoscope system including the endoscope and an external apparatus to which the endoscope is connected, in which the external apparatus includes an external power supply circuit configured to supply power to the power supply circuit of the endoscope and an external power supply restriction circuit configured to restrict a power supply from the external power supply circuit to the power supply circuit according to the temperature of the substrate measured by the temperature sensor of the endoscope.

DETAILED DESCRIPTION OF THE PREFERRED EMBODIMENTS

Figure 2:
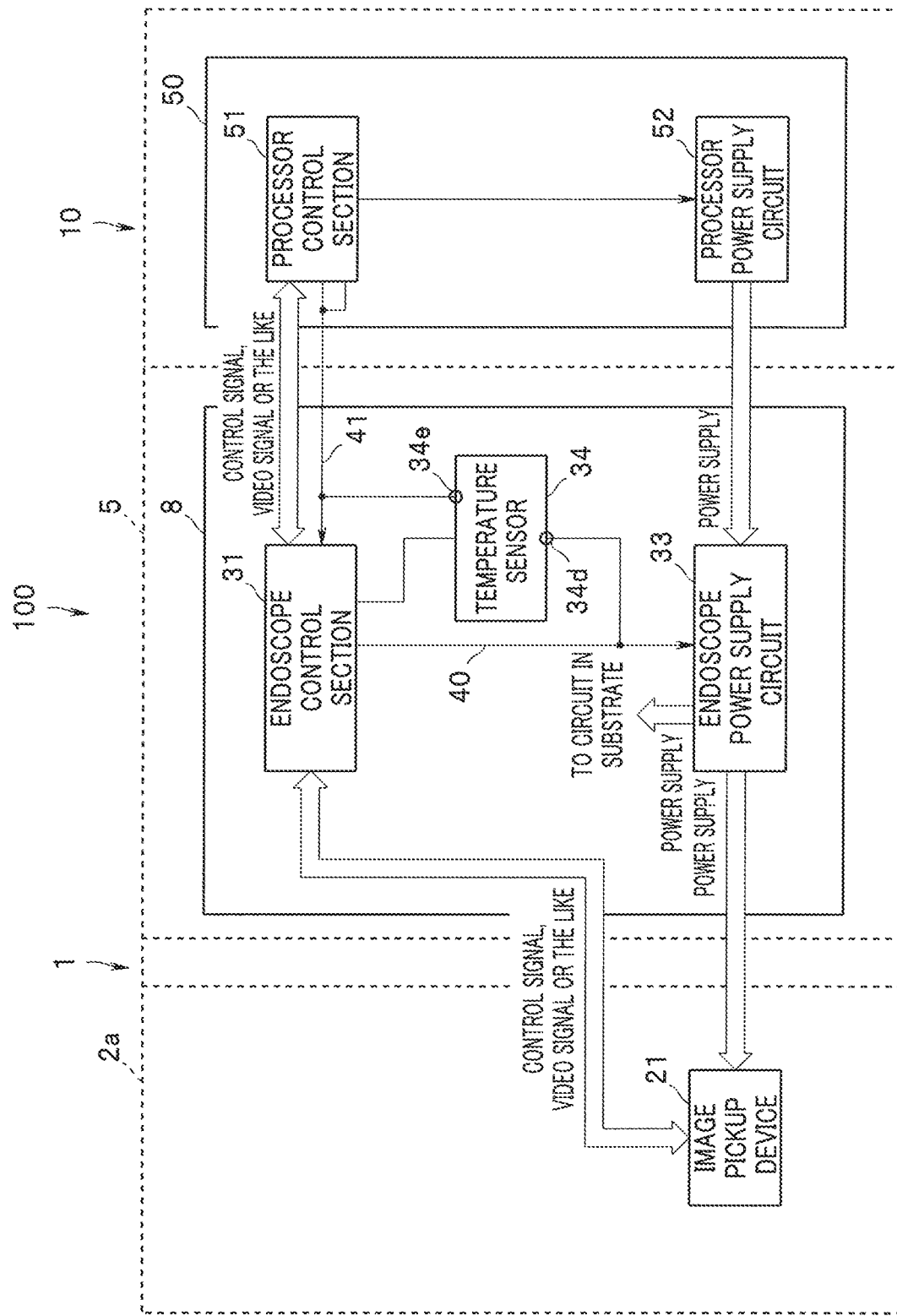
FIG. 2 is a block diagram mainly illustrating a power supply control system of the endoscope system.
Figure 3:
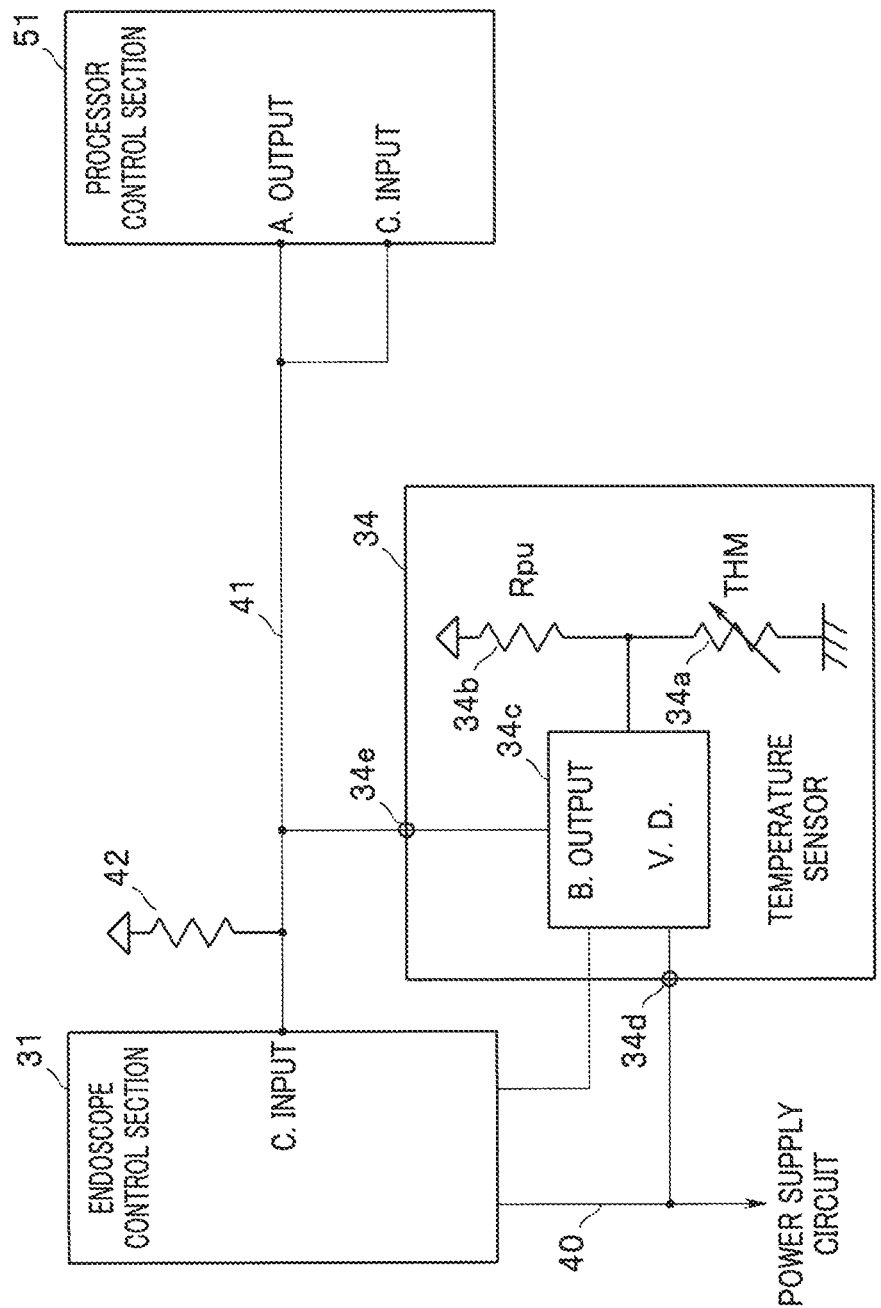
FIG. 3 is a circuit diagram for transmitting temperature detection information to a processor control section.
Figure 4:
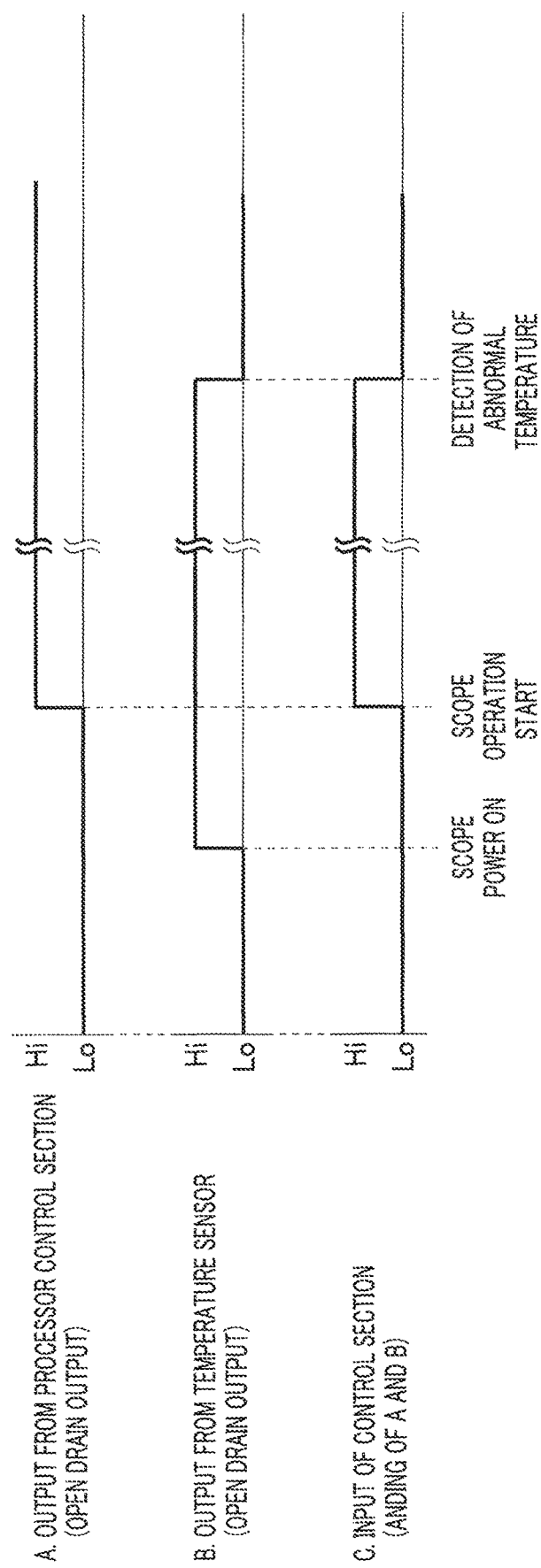
FIG. 4 is an explanatory diagram illustrating a relationship between a drive signal for the endoscope and output from a temperature sensor.
Figure 5:
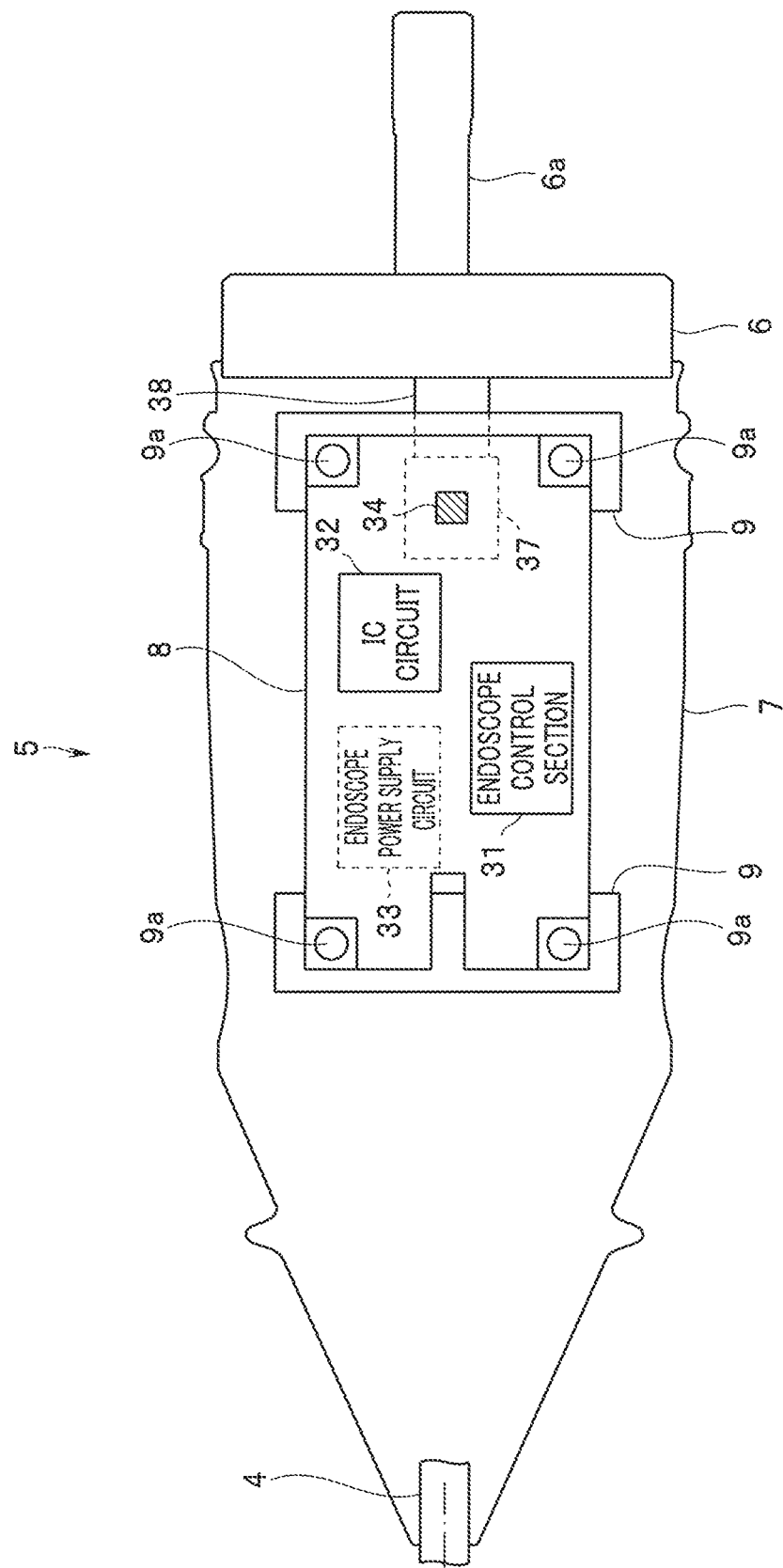
FIG. 5 is a schematic view illustrating an arrangement of the temperature sensor on a connector substrate of an endoscope connector.
Figure 6:
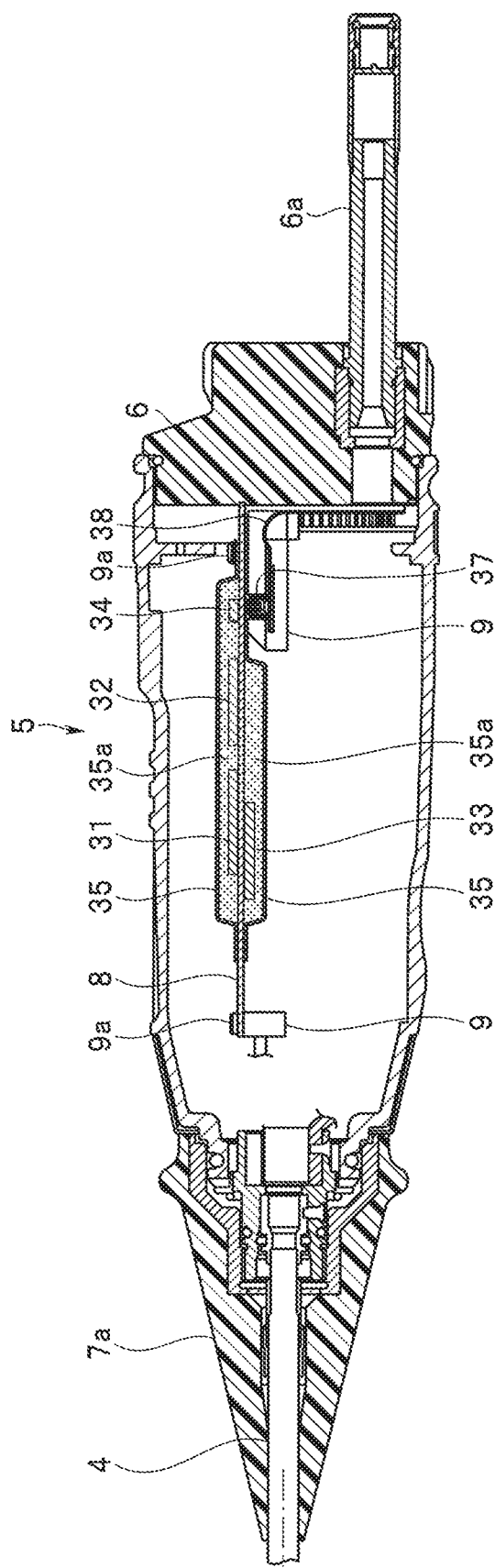
FIG. 6 is a cross-sectional view of main parts of the endoscope connector.
Figure 7:
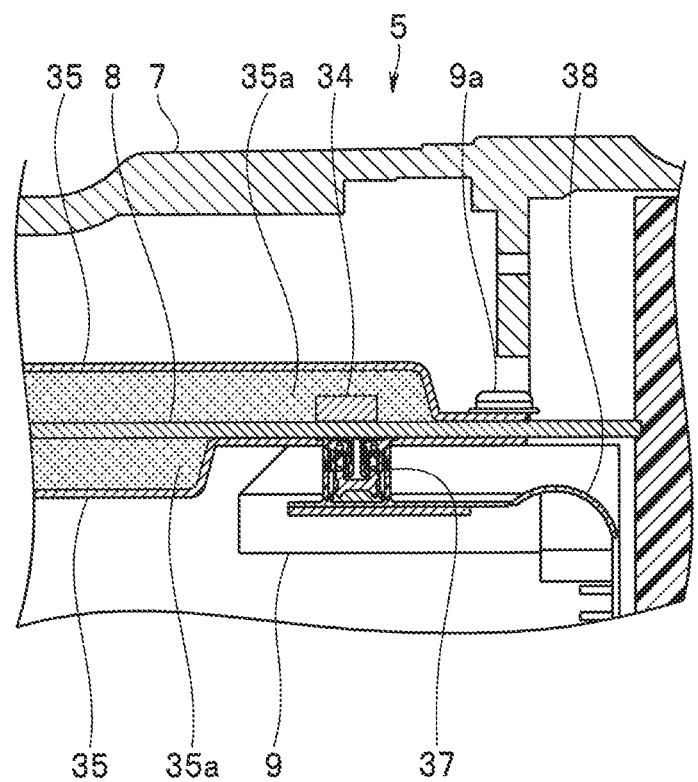
FIG. 7 is an enlarged cross-sectional view illustrating main parts of the connector substrate.
Figure 8:
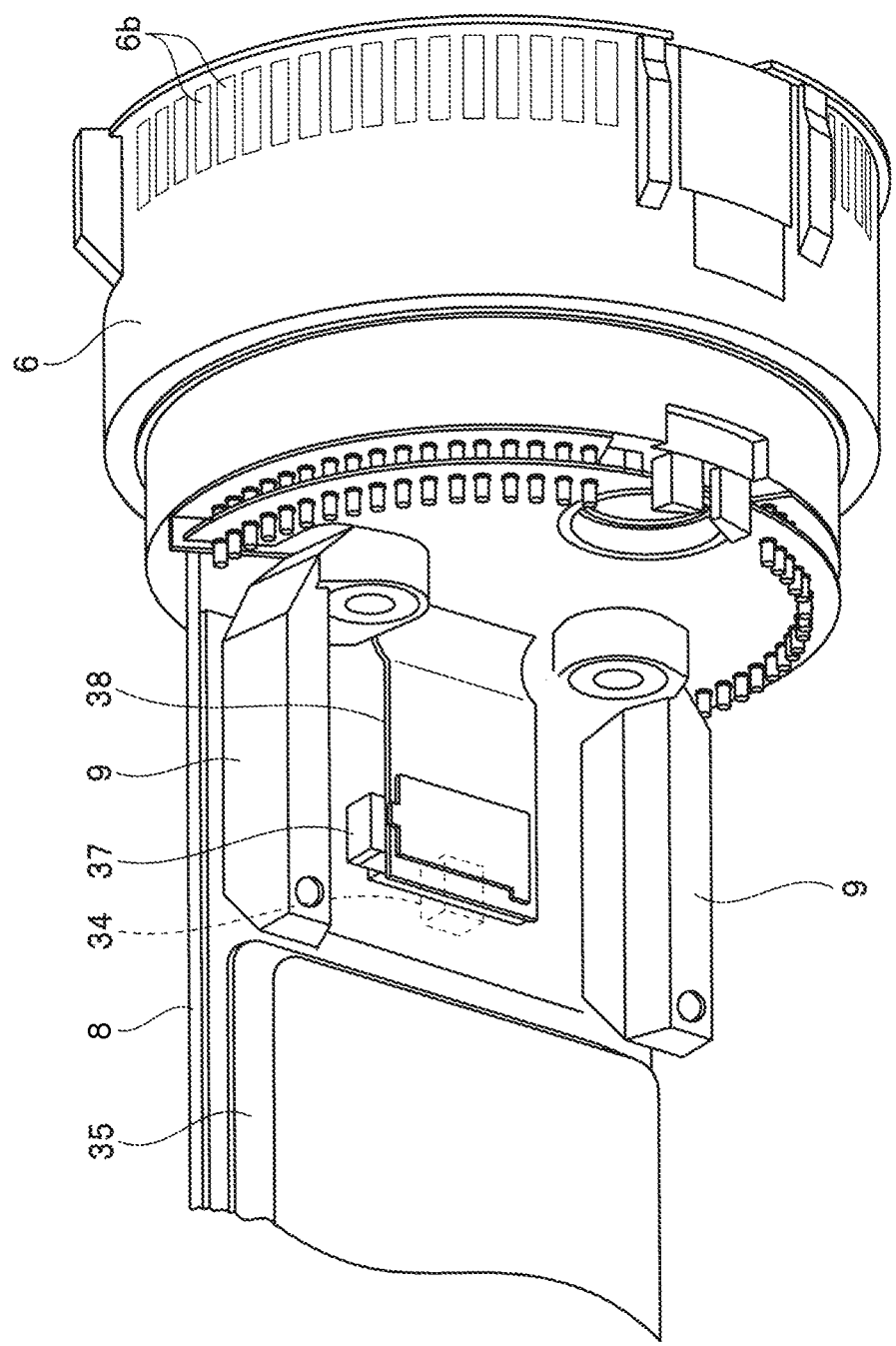
FIG. 8 is a perspective view illustrating main parts of the endoscope connector with an exterior member removed.
Figure 9:
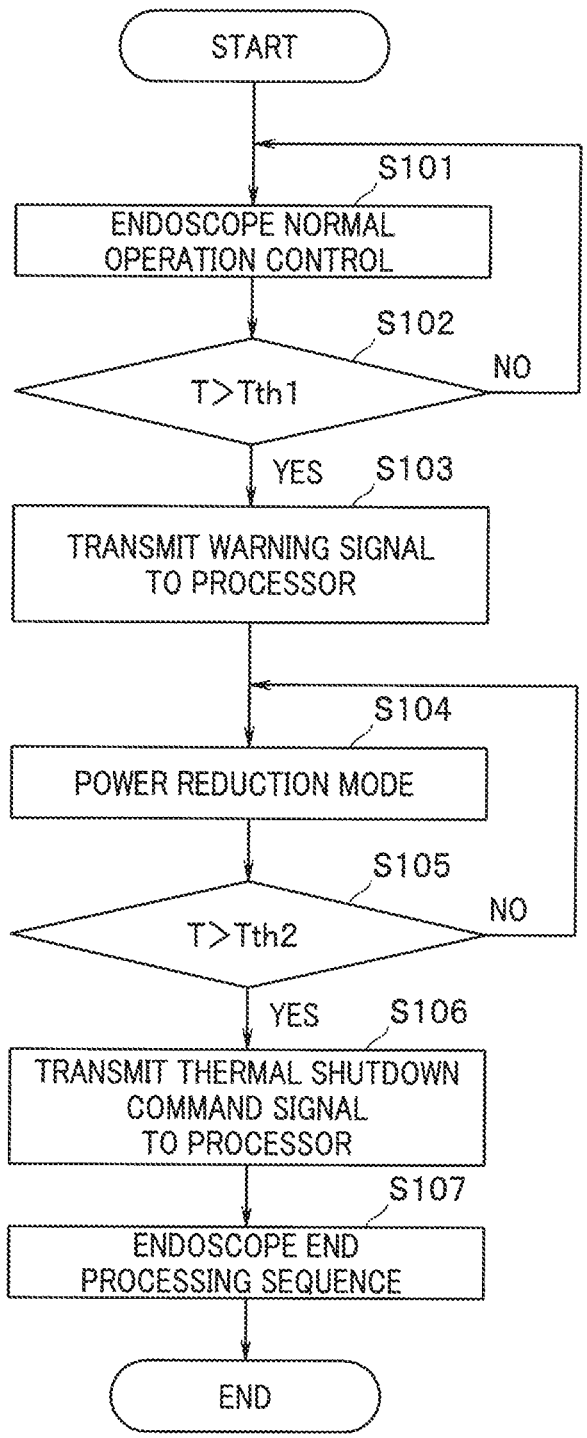
FIG. 9 is a flowchart illustrating an endoscope power supply control routine.
Figure 10:
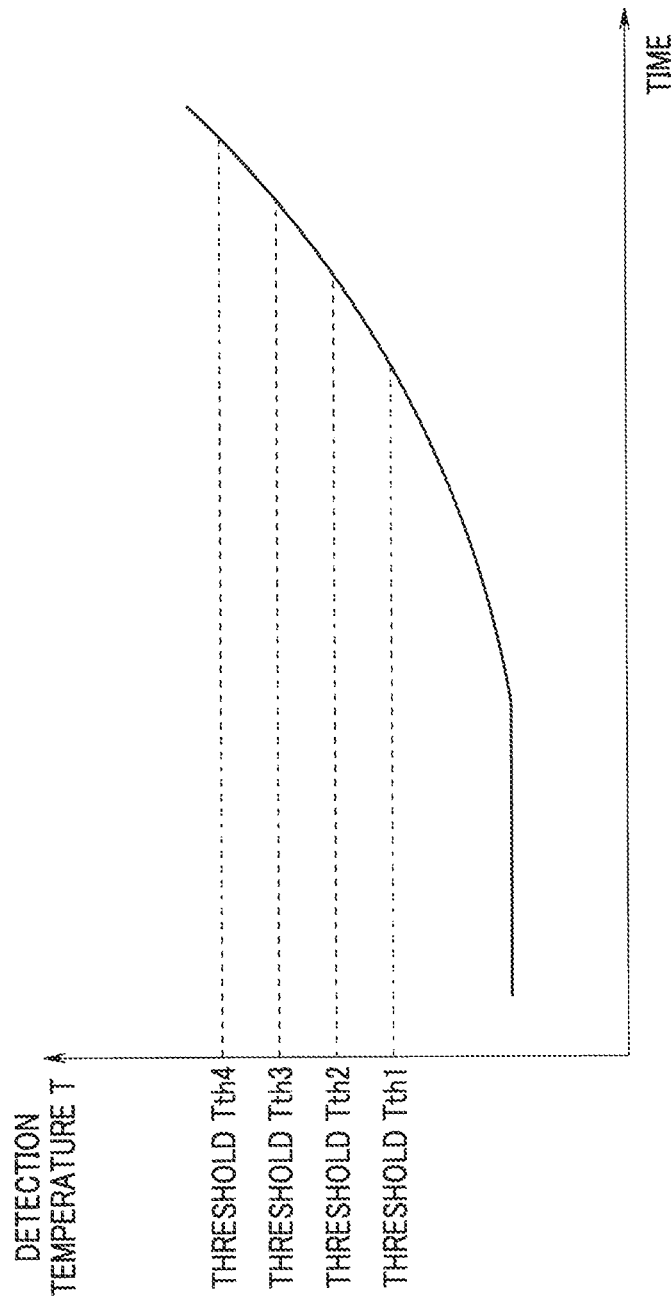
FIG. 10 is an explanatory diagram illustrating a relationship between a detection temperature and each threshold.
Figure 11:
FIG. 11 is a diagram illustrating control contents in a power reduction mode.

Hereinafter, embodiments of the present invention will be described with reference to the accompanying drawings. The drawings relate to an embodiment of the present invention, in which FIG. 1 is a schematic configuration diagram of an endoscope system, FIG. 2 is a block diagram mainly illustrating a power supply control system of the endoscope system, FIG. 3 is a circuit diagram for transmitting temperature sensor detection information to a processor control section, FIG. 4 is an explanatory diagram illustrating a relationship between a drive signal for the endoscope and output from a temperature sensor, FIG. 5 is a schematic view illustrating an arrangement of the temperature sensor on a connector substrate of an endoscope connector, FIG. 6 is a cross-sectional view of main parts of the endoscope connector, FIG. 7 is an enlarged cross-sectional view illustrating main parts of the connector substrate, FIG. 8 is a perspective view illustrating main parts of the endoscope connector with an exterior member removed, FIG. 9 is a flowchart illustrating an endoscope power supply control routine, FIG. 10 is an explanatory diagram illustrating a relationship between a detection temperature and each threshold, and FIG. 11 is a diagram illustrating control contents in a power reduction mode.

Figure 1:
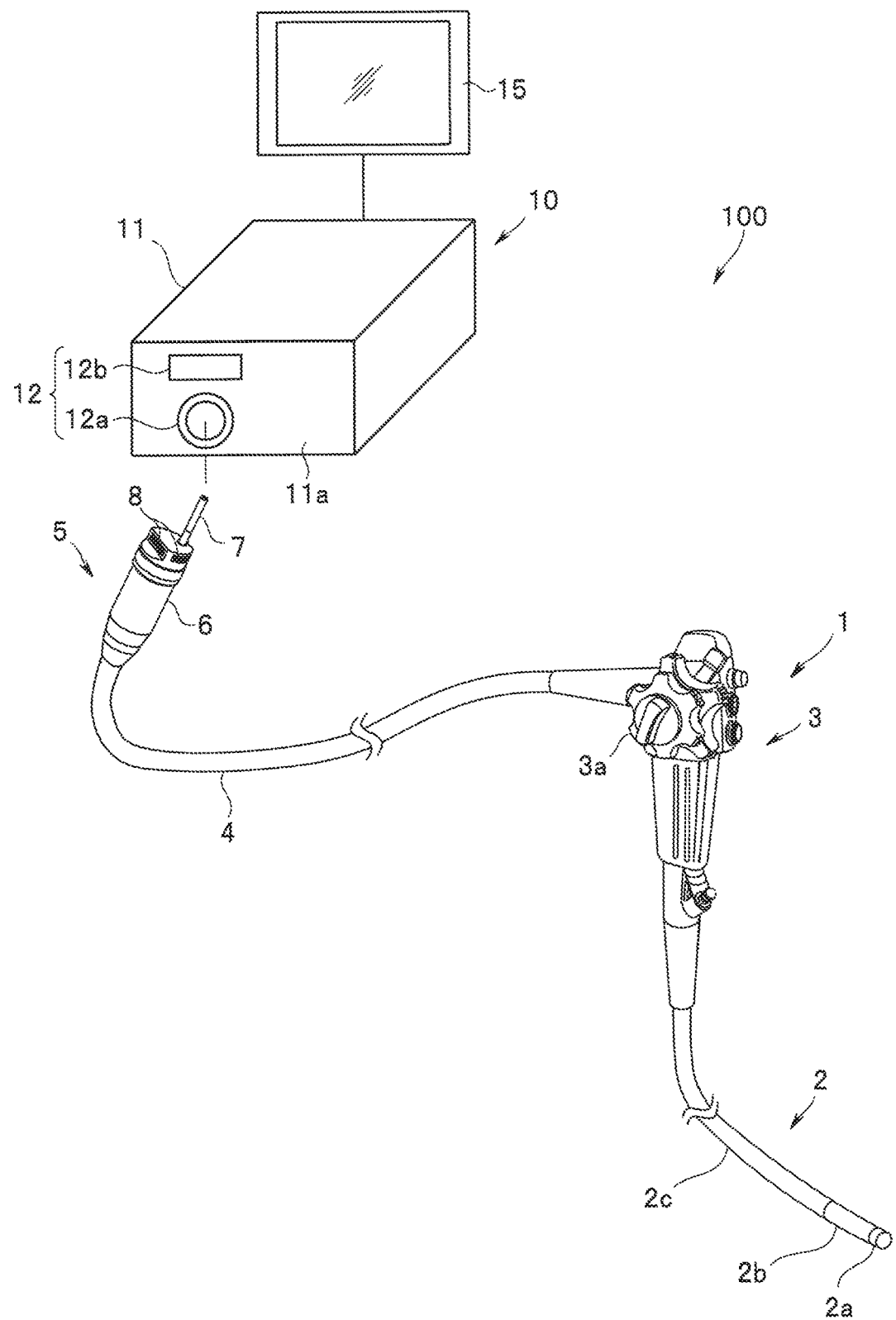
FIG. 1 is a schematic configuration diagram of an endoscope system.

An endoscope system 100 shown in FIG. 1 is constructed of an endoscope configured to pick up an image of an object inside a subject and output an image pickup signal and a light source integrated processor 10 as an external apparatus to which the endoscope 1 is connected and integrally provided with a function as a light source configured to supply illumination light for illuminating the object to the endoscope 1 and a function as a processor configured to process the image pickup signal outputted from the endoscope 1 and output a video signal. A monitor 15 configured to display an image according to the video signal outputted from the processor 10 is connected to the processor 10.

The endoscope 1 is constructed of an elongated insertion portion 2 to be inserted into the subject, an operation portion 3 provided at a rear end of the insertion portion 2 and configured to also function as a grasping portion and perform various operations and a universal cord 4 that extends from the operation portion 3. The endoscope 1 is made attachable/detachable to/from the processor 10 by an endoscope connector 5 as a connector provided at an end portion of the universal cord 4.

The insertion portion 2 is constructed by connecting a rigid distal end portion 2a provided on a distal end side, a freely bendable bending portion 2b connected to a rear end of the distal end portion 2a and a flexible tube 2c having flexibility and provided from a rear end of the bending portion. 2b to a front end of the operation portion 3.

Note that the distal end portion 2a is provided with an illumination optical system configured to irradiate a region to be observed with illumination light and an objective optical system configured to take in reflected light from the region to be observed, and an image pickup device 21 (see FIG. 2) is disposed at an image forming position of the objective optical system. A plurality of bending pieces are disposed at the bending portion 2b and by driving the plurality of bending pieces with bending wires connected to a bending operation knob 3a provided at the operation portion 3, it is possible to bend the bending portion 2b in a desired direction.

As shown, for example, in FIG. 5 to FIG. 8, the endoscope connector 5 is constructed of a plug portion 6 attachable/detachable to/from the processor 10, an exterior case 7 interposed between the plug portion 6 and the universal cord 4 and a connector substrate 8 fixed inside the exterior case 7.

The plug portion 6 has a substantially columnar shape, part of which is planarly cut out, and a light guide 6a protrudes from a proximal end face of the plug portion 6. A plurality of electric contacts 6b are provided in an accurate portion and a plane portion of the plug portion 6, and the endoscope 1 is configured to input/output various control signals, output a video signal and input power or the like to/from the processor 10 via the electric contacts 6b.

The exterior case 7 is constructed of a part having a substantially cylindrical shape. A proximal end side of the universal cord 4 is liquid-tightly connected to a distal end side of the exterior case 7 via a bending prevention portion 7a. The plug portion 6 is liquid-tightly connected to the proximal end side of the exterior case 7.

The connector substrate 8 is constructed, for example, of a plate-shaped substrate extending from the distal end side to the proximal end side within the exterior case 7. The connector substrate 8 is fixed to a pair of brackets 9 protruding inwardly from the distal end side and the proximal end side of the exterior case 7 via screws 9a.

As shown in FIGS. 5 and 6, various electronic parts such as an endoscope control section 31 as an endoscope control circuit for centrally controlling the entire endoscope 1 and an IC circuit 32, an endoscope power supply circuit 33 as a power supply circuit for supplying power from the processor 10 to the respective components of the endoscope 1 and a temperature sensor 34 for detecting a temperature T of the connector substrate 8 as a temperature inside the endoscope connector 5 or the like are mounted on both sides of the connector substrate 8.

Here, the endoscope control section 31 is constructed of an integrated circuit such as a field programmable gate array (FPGA). Note that the endoscope control section 31 may also be implemented by a computer made up of one or a plurality of processors, a logical circuit, a memory, an input/output interface and a computer-readable recording medium or the like. In this case, the endoscope control section 31 can operate according to a program stored, for example, in a memory (not shown) and control each component.

Covers 35 for covering the above-described respective mounted components (endoscope control section 31, IC circuit. 32, endoscope power supply circuit 33 and temperature sensor 34 or the like) are provided on both sides of the connector substrate 8. Furthermore, a filler 35a is filled inside the covers 35. The respective components mounted on the connector substrate 8 are liquid-tightly sealed with the filler 35a.

Furthermore, the connector substrate 8 is provided with a B to B connector (board to board connector) 37 as a connector section for electrically connecting a flexible printed circuit board 38 extending from the plug portion 6 to the connector substrate 8. Here, the flexible printed circuit board 38 is constructed by including a plurality of signal lines electrically connected to each electric contact 6b of the plug portion 6. In the present embodiment, in order to allow the connector substrate 8 to be replaced during maintenance of the endoscope 1, the B to B connector 37 is configured so as to connect the connector substrate 8 and the flexible printed circuit board 38 outside the covers 35 (in other words, without being sealed with the filler 35a).

The processor 10 incorporates a processor substrate 50. Various electronic parts including a processor control section 51 having a function as the external power supply restriction circuit for centrally controlling the endoscope system 100 are mounted on the processor substrate 50. Furthermore, a processor power supply circuit 52, as an external power supply circuit for supplying power to the respective components of the processor 10 and the endoscope 1, and the like are mounted on the processor substrate 50 (see FIG. 2). The processor 10 further incorporates a light source section (not shown) for supplying illumination light to the endoscope 1. Here, the processor control section 51 is constructed of an integrated circuit such as a field programmable gate array (FPGA). Note that the processor control section 51 may also operate according to a program stored in a memory (not shown) and control the respective components.

The processor 10 is provided with connectors 12a and 12b on a front face 11a of a case 11. The connectors 12a and 12b are connectors on a receptacle side used according to a type of the endoscope, and FIG. 1 illustrates an example where the endoscope connector 5 of the endoscope 1 is detachably connected to the connector 12a.

The connector 12a is provided with electric contacts (receptacle contacts) corresponding to the plurality of respective electric contacts 6b of the endoscope connector 5 within an engagement part with which the plug portion 6 of the endoscope connector 5 engages. The connector 12b is likewise provided with a plurality of electric contacts (receptacle contacts) corresponding to the electric contacts 6b on the endoscope 1 side.

In the example in FIG. 1, when the plug portion 6 of the endoscope connector 5 is inserted into the engagement part of the connector 12a, the respective contacts are contacted and electrical connection between the endoscope 1 and the processor 10 is made. This makes it possible to send and receive various signals between the endoscope 1 (endoscope control section 31) and the processor 10 (processor control section 51) and supply power from the processor 10 to the endoscope 1. Furthermore, the insertion of the aforementioned plug portion 6 causes the light guide 6a protruding from the distal end face of the plug portion 6 to be optically connected to the light source section of the processor 10. This causes the light guide 6a to guide illumination light from the processor 10 to the distal end portion 2a of the endoscope 1, making it possible to irradiate a subject with the illumination light from the illumination optical system of the distal end portion 2a.

The illumination light radiated onto the subject is reflected by the subject and the reflected light (return light) is imaged on a light receiving surface of the image pickup device 21 incorporated in the distal end portion 2a of the endoscope 1 as an optical image. The image pickup device 21 in the distal end portion 2a is driven and controlled by the endoscope control section 31 incorporated in the endoscope connector 5, converts the optical image of the subject to an electric signal (video signal) and outputs the electric signal to the processor 10.

The processor control section 51 performs various kinds of signal processing on the video signal from the endoscope 1 and displays the image of the subject on a display screen of the monitor 15.

Next, the power supply system in the endoscope system 100 configured as described above will be described with reference to FIG. 2 or the like.

The endoscope system 100 of the present embodiment is configured such that when the endoscope connector 5 is connected to the processor 10 and an ON signal from the processor control section 51 is inputted to the processor power supply circuit 52, power is supplied from the processor power supply circuit 52 to the endoscope power supply circuit 33.

The endoscope system 100 is also configured such that when an ON signal from the endoscope control section 31 is inputted to the endoscope power supply circuit 33, power is supplied from the endoscope power supply circuit 33 to the respective components on the connector substrate 8 and power is supplied to the image pickup device 21 or the like disposed in the distal end portion 2a.

In this case, the endoscope connector 5 is configured so as to restrict a power supply from the endoscope power supply circuit 33 according to a temperature of the connector substrate 8 detected by the temperature sensor 34 as a measure for preventing a temperature rise inside the endoscope connector 5.

The power supply is restricted basically by the endoscope control section 31 controlling the endoscope power supply circuit 33 or the like according to output from the temperature sensor 34. In other words, the endoscope control section 31 implements the function as the power supply restriction circuit in the present embodiment.

In this case, the temperature sensor 34 is constructed, for example, of a thermistor type temperature sensor. In other words, as shown, for example, in FIG. 3, the temperature sensor 34 is constructed by including a thermistor 34a as a temperature detection section connected to a constant voltage source (endoscope power supply circuit 33) via a pullup resistor 34b and a voltage detection circuit 34c configured to detect an output voltage (thermistor output) Vth that changes according to a resistance ratio between the thermistor 34a and the pullup resistor 34b. The voltage detection circuit 34c is configured so as to output a temperature signal according to a thermistor output Vth to the endoscope control section 31 as a temperature T of the connector substrate 8.

Here, as shown, for example, in FIG. 5 to FIG. 8, the temperature sensor 34 of the present embodiment is disposed in the vicinity of the B to B connector 37 on the connector substrate 8 and is configured to detect a temperature at the position as a temperature T of the connector substrate 8.

When a temperature signal from the temperature sensor 34 is inputted, the endoscope control section 31 restricts the power supply to each component of the endoscope 1 from the endoscope power supply circuit 33 in stages as the temperature T of the connector substrate 8 rises.

More specifically, when the temperature T of the connector substrate 8 is determined to have exceeded a first set temperature Tth1 set in advance, the endoscope control section 31 exercises energy saving mode control to suppress power consumption at the endoscope connector 5.

Here, the first set temperature Tth1 is, for example, a level where no temperature rise of the connector substrate 8 is expected in a normal operating temperature environment, but Tth1 is a temperature at which it is preferable to make a predetermined warning or the like in preparation for a temperature rise, and Tth1 is set based on an experiment or simulation or the like.

When the temperature T of the connector substrate 8 is determined to have exceeded a second set temperature Tth2 set in advance, the endoscope control section 31 turns off the endoscope power supply circuit 33 according to a shutdown sequence of the endoscope 1.

Here, the second set temperature Tth2 is, for example, a temperature higher than the first set temperature Tth1 and is a temperature which may exceed a device rating of the endoscope connector 5 or product exterior case temperature standard and is set based on an experiment or simulation or the like.

The power supply control by such an endoscope control section 31 is exercised according to a flowchart of an endoscope power supply control routine shown, for example, in FIG. 9.

When this routine starts, the endoscope control section 31 first causes the endoscope 1 to operate through a predetermined normal operation set in advance in step S101. In other words, the endoscope control section 31 outputs a predetermined control signal to each component of the endoscope 1. For example, the endoscope control section 31 outputs a control signal including an ON signal to the endoscope power supply circuit 33, and exercises power supply control at a predetermined output voltage on each component from the endoscope power supply circuit 33. For example, the endoscope control section 31 outputs a drive signal or the like for causing the image pickup device 21 to perform image pickup at a frame rate set in advance.

Furthermore, after performing, for example, image processing or the like on a video signal inputted from the image pickup device 21, the endoscope control section 31 outputs the video signal to the processor 10 with a predetermined output amplitude.

After proceeding from step S101 to step S102, the endoscope control section 31 examines whether the temperature T of the connector substrate 8 detected by the temperature sensor 34 exceeds the first set temperature Tth1 set in advance.

When it is determined in step S102 that the temperature T has not exceeded the first set temperature Tth1, the endoscope control section 31 returns to step S101 and continues normal operation control of the endoscope 1.

On the other hand, when it is determined in step S102 that the temperature T has exceeded the first set temperature Tth1, the endoscope control section 31 proceeds to step S103 and transmits to the processor 10 a warning signal for warning a user or the like.

After proceeding from step S103 to step S104, the endoscope control section 31 exercises power reduction mode control for suppressing power consumption in the endoscope connector 5 in order to suppress a temperature rise inside the endoscope connector 5.

As the power reduction mode control, as shown, for example, in FIG. 11, it is preferable to change control contents in order starting with an item with a least influence on image quality of the endoscope image. In other words, when the temperature T continues to rise, the endoscope control section 31 changes the control contents, for example, in the following order.

When the power reduction mode control starts, the endoscope control section 31 exercises control to lower a switching frequency of the endoscope power supply circuit 33 first.

Next, the endoscope control section 31 exercises control to lower an output amplitude of the video signal to be outputted to the processor 10.

Next, the endoscope control section 31 exercises control to lower an output voltage to the image pickup unit including the image pickup device 21.

Next, the endoscope control section 31 outputs a control signal to the processor 10 and exercises control to restrict a power supply from the processor power supply circuit 52.

Next, the endoscope control section 31 reduces or stops image correction processing on the video signal being executed by the endoscope control section 31.

Next, the endoscope control section 31 outputs a control signal to the image pickup device 21 and exercises control to lower the frame rate of the image pickup device 21.

After proceeding from step S104 to step S105, the endoscope control section 31 examines whether the temperature T of the connector substrate 8 detected by the temperature sensor 34 has exceeded the second set temperature Tth2 set in advance.

When it is determined in step S105 that the temperature T has not exceeded the second set temperature Ith2, the endoscope control section 31 returns to step S104 and continues the power reduction mode control of the endoscope 1.

On the other hand, when it is determined in step S105 that the temperature T has exceeded the second set temperature Tth2, the endoscope control section 31 proceeds to step S106 and transmits to the processor 10 a command signal for performing thermal shutdown due to an abnormal temperature rise of the endoscope connector 5.

In next step S107, after performing an endoscope end processing sequence for causing the endoscope 1 to end due to a temperature abnormality, the endoscope control section 31 exits the routine.

Thus, the endoscope 1 of the present embodiment can appropriately manage the temperature of the endoscope connector 5 in the endoscope 1 by providing the temperature sensor 34 to directly measure the temperature of the connector substrate 8 on the connector substrate 8 of the endoscope connector 5 to be connected to the processor 10, restricting the power supply (in other words, limiting and stopping the power supply) from the endoscope power supply circuit 33 according to the measured temperature of the connector substrate 8 (in other words, the endoscope connector 5).

As a scheme fir detecting a temperature of the connector substrate 8 in this case, for example, a monitoring circuit may be adopted, which estimates the temperature of the connector substrate 8 based on a rise of the supply voltage or the current to be supplied from the endoscope power supply circuit 33 to each component of the endoscope 1, but such a scheme may complicate calculations and it may be difficult to reliably detect a temperature rise. By contrast, in the present embodiment, it is possible to implement temperature detection of the connector substrate 8 with a simple configuration by adopting the thermistor type temperature sensor 34 using the thermistor 34a as the temperature detection section.

By detecting the temperature T in the vicinity of the B to B connector 37, which is not sealed with the filler 35a using the aforementioned temperature sensor 34 as the temperature of the connector substrate 8, even if a temperature rise occurs in the B to B connector 37 due to a short circuit or the like, it is possible to accurately suppress the temperature rise of the connector substrate 8.

Here, as a countermeasure when some trouble occurs in the endoscope control section 31, the endoscope 1 of the present embodiment can also cause the temperature sensor 34 to function as the power supply restriction circuit that connects an open drain output terminal 34d of the temperature sensor 34 to a signal line 40 that outputs a signal for controlling ON/OFF from the endoscope control section 31 to the endoscope power supply circuit 33 as shown, for example, in FIG. 2 and directly turns off the endoscope power supply circuit 33 when the temperature T of the connector substrate 8 becomes a third set temperature Tth3 (see FIG. 10), which is higher than the second set temperature Tth2.

In this case, for example, as a control signal from the endoscope control section 31, when a high-level signal is outputted when the endoscope power supply circuit 33 is turned on and a low-level signal is outputted when the endoscope power supply circuit 33 is turned off, the temperature sensor 34 draws in current from the signal line 40 when the temperature T exceeds the third set temperature Ith3, and it is thereby possible to lower the voltage of the control signal from high level to low level, and turn off the endoscope power supply circuit 33.

As a further trouble countermeasure, as shown, for example, in FIGS. 2 and 3, the endoscope system 100 of the present embodiment can connect the open drain output terminal 34e of the temperature sensor 34 to one of signal lines connecting the endoscope control section 31 and the processor control section 51 and can also cause the temperature sensor 34 to function as the power supply restriction circuit that causes the processor control section 51 to turn off the power supply from the processor power supply circuit 52 to the endoscope power supply circuit 33 when the temperature T of the connector substrate 8 becomes a fourth set temperature Tth4 (see FIG. 10) higher than the third set temperature Ith3.

In this case, it is possible to suitably adopt, for example, a signal line 41 for a control signal (enable signal), the level of which becomes high when communication between the endoscope control section 31 and the processor control section 51 is established and low when communication is interrupted. The signal line 41 is connected to the endoscope power supply circuit 33 via a pullup resistor 4:2 inside the endoscope 1. The processor control section 51 includes an input terminal for monitoring a control signal in addition to the output terminal for the signal line 41. When the level of the control signal becomes low from high, the processor control section 51 detects that communication with the endoscope control section 31 is interrupted and turns off the power supply from the processor power supply circuit 52 to the endoscope power supply circuit 33.

For such a signal line 41, when the temperature T exceeds the fourth set temperature Tth4, the temperature sensor 34 draws in current from the signal line 41 to thereby lower the voltage of the control signal from high level to low level, and can cause the processor control section 51 to turn off the power supply from the processor power supply circuit 52 to the endoscope power supply circuit 33 (see FIG. 4).

Even if the temperature control by the endoscope control section 31 on the connector substrate 8 becomes impossible, these configurations can accurately protect the connector substrate 8 (endoscope connector 5) from heat damage.

Figure 12:
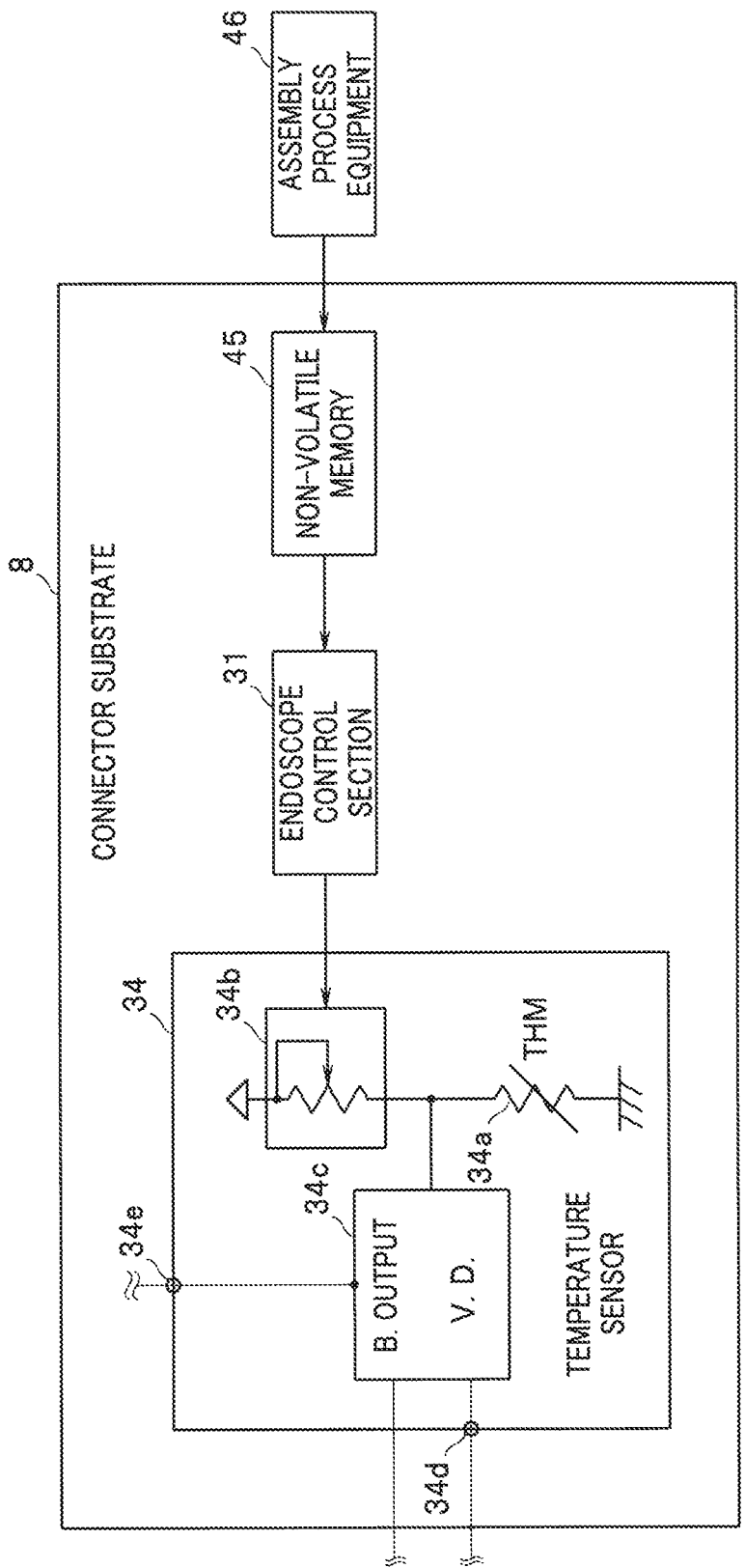
FIG. 12 relates to a first modification and is a block diagram illustrating main parts of a scope substrate on which a temperature sensor provided with a variable resistor is mounted.

Here, as shown, for example, in FIG. 12, it is also possible to adopt a variable resistor for the pullup resistor 34b used for the temperature sensor 34. In this case, it is possible to use assembly process equipment 46 to store resistance values corresponding to the type of the endoscope 1 and individual differences or the like in advance in a non-volatile memory 45 provided in the connector substrate 8 and cause the endoscope control section 31 to set a resistance value of the pullup resistor 34b when starting the endoscope 1 to thereby enable more appropriate temperature management.

Figure 13:
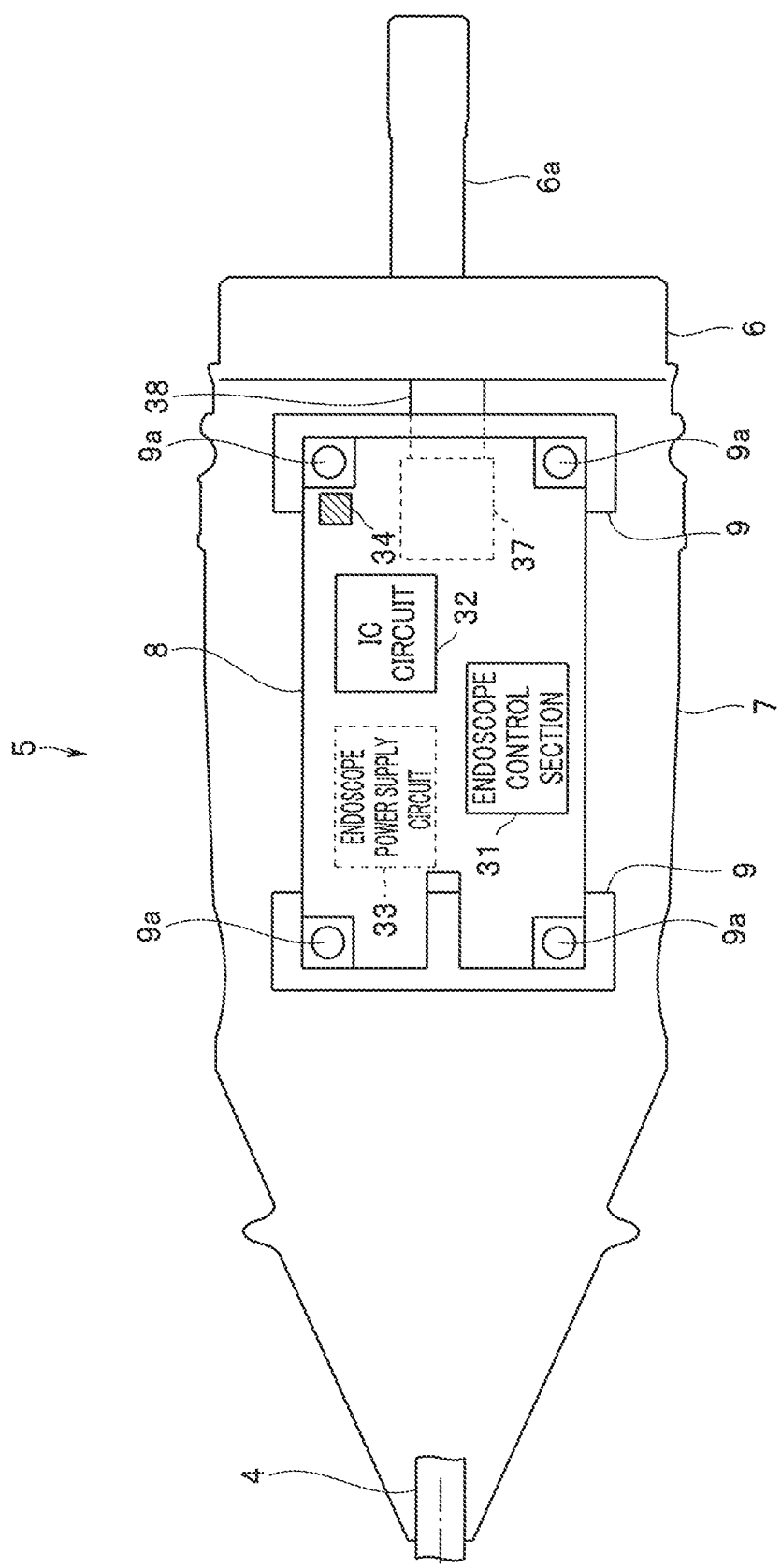
FIG. 13 relates to a second modification and is a schematic view illustrating an arrangement of the temperature sensor on a connector substrate of an endoscope connector.

For example, as shown in FIG. 13, the temperature sensor 34 can be disposed at a mechanical contact portion of the connector substrate 8 (e.g., fastening portion by the screw 9a between the connector substrate 8 and the bracket 9), which is assumed to be a heat transfer path of the endoscope connector 5 for the exterior case 7.

Such a configuration allows the temperature of the exterior case 7 of the endoscope connector 5 to be controlled more accurately.

Figure 14:
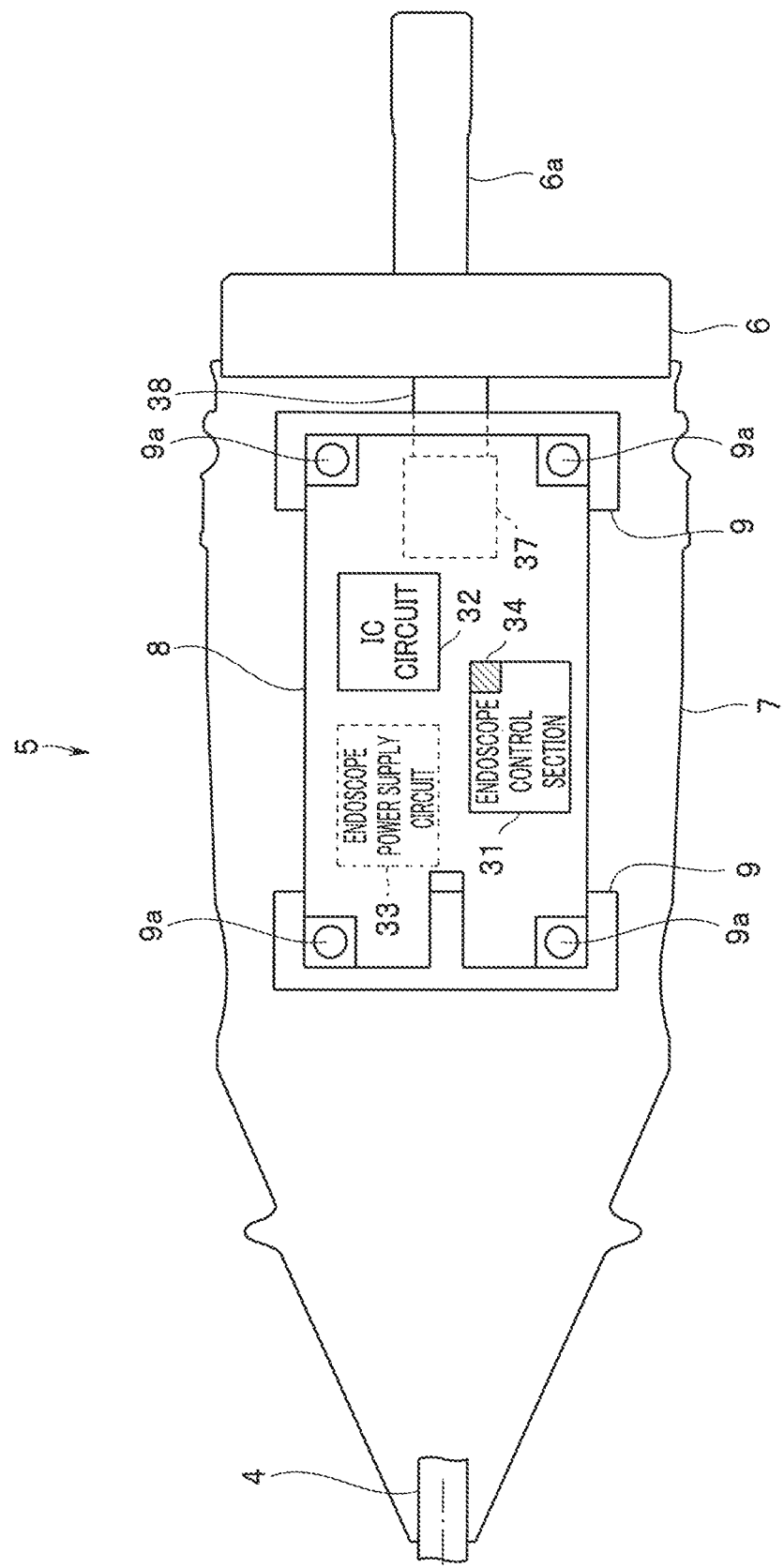
FIG. 14 relates to a third modification and is a schematic view illustrating an arrangement of the temperature sensor on a connector substrate of an endoscope connector.

For example, when the endoscope control section 31 is made up of an FPGA, the endoscope control section 31 can be caused to include the function as the temperature sensor 34 as shown in FIG. 14.

Such a configuration does not require any additional wiring or circuit, and can thereby simplify the configuration of the connector substrate 8.

Figure 15:
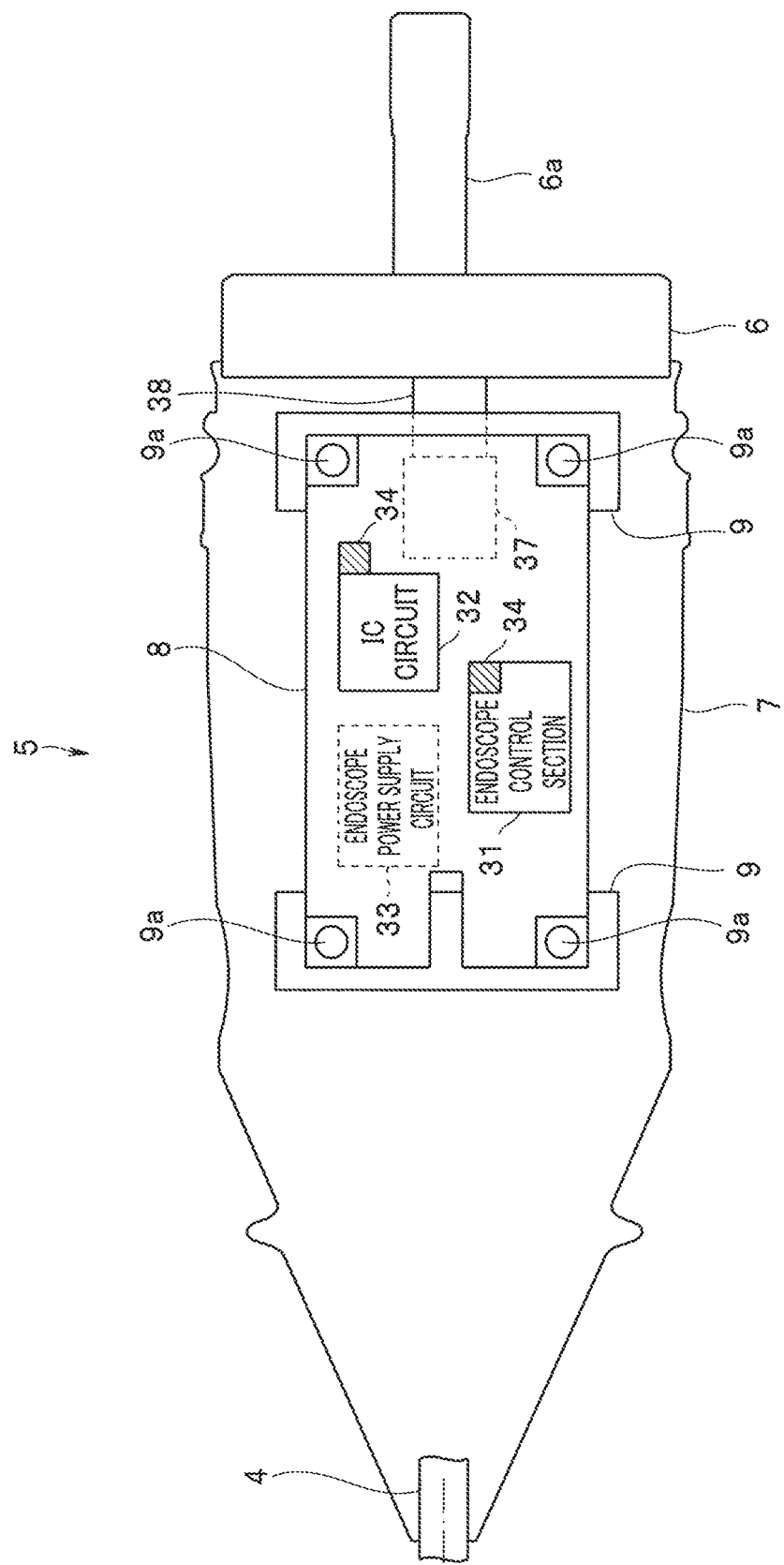
FIG. 15 relates to a fourth modification and is a schematic view illustrating an arrangement of the temperature sensor on a connector substrate of an endoscope connector.

Furthermore, as shown, for, example, in FIG. 15, the temperature sensor 34 can be provided in the vicinity of the IC circuit 32 or the like, which can be a heat source on the connector substrate 8.

Note that the present invention is not limited to the embodiments described so far, but various modifications or changes can be made and such modifications or changes also fall within the technical scope of the present invention.

What is claimed is:

1. An endoscope comprising:
an insertion portion comprising an image pickup device;
a cord having a distal end and a proximal end;
an operation portion connected to the distal end of the cord; and
a connector connected to the proximal end of the cord, the connector comprising:
an exterior member configured to be detachably connected to an external apparatus; and
a substrate provided inside the exterior member, the substrate comprising:
a power supply circuit configured to supply a power provided from the external apparatus to the image pickup device;
a control circuit configured to receive a control signal from the external apparatus and the image pickup device; and
a temperature sensor configured to measure a temperature of the substrate,
wherein the control circuit is configured to restrict the power supplied by the power supply circuit according to the temperature of the substrate measured by the temperature sensor.

2. The endoscope according to claim 1, wherein control circuit is configured to suppress power consumption in the substrate in response to the temperature of the substrate measured by the temperature sensor exceeding a first set temperature set in advance.

3. The endoscope according to claim 2, wherein the control circuit is configured to turn off the power supplied by the power supply circuit in response to the temperature of the substrate measured by the temperature sensor exceeding a second set temperature higher than the first set temperature.

4. The endoscope according to claim 3,
wherein the temperature sensor is configured to output a signal to turn off the power supplied by the power supply circuit in response to the temperature of the substrate measured by the temperature sensor exceeding a third set temperature higher than the second set temperature.

5. The endoscope according to claim 2, wherein, in response to the temperature of the substrate measured by the temperature sensor exceeding the first set temperature, the control circuit is configured to suppress power consumption in the substrate by controlling the power supply circuit to decrease a switching frequency.

6. The endoscope according to claim 1 wherein the temperature sensor is provided at a portion of the connector configured to connect the substrate to a signal line.

7. The endoscope according to claim 1, wherein the temperature sensor is provided at a predetermined position having a temperature correlation between the substrate and the exterior member.

8. The endoscope according to claim 1, wherein the temperature sensor is provided at a mechanical connection portion connecting the exterior member and the substrate.

9. The endoscope according to claim 1, wherein the temperature sensor is provided at a part of the substrate that is a heat source on the substrate.

10. The endoscope according to claim 1,
wherein the control circuit comprises a field programmable gate array, and
wherein the temperature sensor is mounted inside the field programmable gate array.

11. The endoscope according to claim 1, wherein the connector further comprises:
a cover covering the substrate; and
a filler filled between the cover and the substrate, wherein the filler covers the temperature sensor.

12. The endoscope according to claim 11,
wherein the connector further comprises a board connector provided on one side of the substrate and configured to connect a substrate to another component, and
wherein the temperature sensor is located on an opposite side of the substrate across from the board connector.

13. The endoscope according to claim 1, wherein the substrate extends along a longitudinal direction of the connector.

14. An endoscope system comprising:
the endoscope according to claim 1; and
the external apparatus to which the exterior member of the connector of the endoscope is detachably connected,
wherein the external apparatus comprises:
an external power supply circuit configured to supply the power to the power supply circuit of the endoscope; and
an external control circuit configured to restrict the power supplied from the external power supply circuit to the power supply circuit based on the temperature of the substrate measured by the temperature sensor of the endoscope.

15. The endoscope system according to claim 14,
wherein the external control circuit is configured to turn off the power supplied from the external power supply circuit to the power supply circuit of the endoscope in response to the temperature of the substrate measured by the temperature sensor of the endoscope exceeds a fourth set temperature set in advance.

16. The endoscope according to claim 14, wherein in response to the temperature of the substrate measured by the temperature sensor exceeding a first set temperature, the control circuit is configured to suppress power consumption in the substrate by performing one or more of the following controls, in the following order:
(i) control the power supply circuit to decrease a switching frequency;
(ii) control an output amplitude of a video signal output by the image pickup device to be lower;
(iii) control the power supply circuit to lower an output voltage to the image pickup device;
(iv) control the external power supply circuit, configured to supply power to the power supply circuit, to restrict the power supplied to the power supply circuit of the endoscope;
(v) reduce or stop image correction processing performed by the control circuit; and
(vi) control the image pickup device to reduce a frame rate of the image pickup device.

17. An endoscope comprising:
an insertion portion comprising an image pickup device;
a substrate provided at a proximal side of the insertion portion;
an endoscope power supply circuit provided on the substrate, wherein the endoscope power supply circuit is configured to supply power to the image pickup device; and
a control circuit provided on the substrate, wherein the control circuit is configured to:
receive a measured temperature of the substrate;
determine whether the measured temperature of the substrate continues to rise above a first temperature; and
control to lower a switching frequency of the endoscope power supply circuit in response to determining that the measured temperature of the substrate continues to rise above the first temperature.

18. The endoscope according to claim 17, wherein in response to the measured temperature of the substrate exceeding the first temperature, the control circuit is configured to suppress power consumption in the substrate by performing one or more of the following controls, in the following order:
(i) control an output amplitude of a video signal output by the image pickup device to be lower;
(ii) control the endoscope power supply circuit to lower an output voltage to the image pickup device;
(iii) control an external power supply circuit configured to supply power to the endoscope power supply circuit to restrict the power supplied to the endoscope power supply circuit;
(iv) reduce or stop image correction processing performed by the control circuit; and
(v) control the image pickup device to reduce a frame rate of the image pickup device.

19. The endoscope according to claim 17, further comprising a temperature sensor configured to measure the temperature of the substrate.

20. The endoscope according to claim 17, wherein the control circuit comprises a field programmable gate array.

* * * * *